United States Patent [19]

Lindt

[11] 4,403,502

[45] Sep. 13, 1983

[54] VISCOMETER FOR CAST FOAMING MATERIALS AND ASSOCIATED METHOD

[75] Inventor: Jan T. Lindt, Pittsburgh, Pa.

[73] Assignee: University of Pittsburgh, Pittsburgh, Pa.

[21] Appl. No.: 240,581

[22] Filed: Mar. 4, 1981

[51] Int. Cl.³ .................... G01N 11/08; G01F 23/28
[52] U.S. Cl. ..................................... 73/55; 73/290 V
[58] Field of Search .............. 73/55, 56, 54, 60.1, 73/290 V; 367/908

[56] References Cited

U.S. PATENT DOCUMENTS

| | | | |
|---|---|---|---|
| 2,315,983 | 4/1943 | Ross et al. | 73/60.1 |
| 3,138,950 | 6/1964 | Welty et al. | 73/55 |
| 3,194,057 | 7/1965 | Richard | 73/55 |
| 3,277,694 | 10/1966 | Cannon et al. | 73/55 |
| 3,283,565 | 11/1966 | Müller et al. | 73/55 |
| 3,360,986 | 1/1968 | Rothschild | 73/56 |
| 3,535,917 | 10/1970 | Blair et al. | 73/55 |
| 3,559,464 | 2/1971 | Foust et al. | 73/55 |
| 4,137,754 | 2/1979 | Colombo et al. | 73/56 |

FOREIGN PATENT DOCUMENTS 531064  2/1977  U.S.S.R. ........................... 73/55

OTHER PUBLICATIONS

*Polyurethane Foam Process Development, A Systems Engineering Approach,* Campbell, G. A., In Journ. of Applied Polymer Sci., vol. 16, pp.1337–1402, 1972.

Primary Examiner—Charles A. Ruehl
Assistant Examiner—Joseph W. Roskos
Attorney, Agent, or Firm—Buell, Blenko, Ziesenheim & Beck

[57] ABSTRACT

A motionless viscometer and associated method for resinous materials including polymeric foams and non-resinous materials includes a reservoir section, a receiver section and an interposed tube. As the foam is expanded the axial pressure within the connecting tube is measured as is the rate of rise of the foam within the receiver element. Shear viscosity and density as functions of time may be determined.

21 Claims, 6 Drawing Figures

VISCOMETER FOR CAST FOAMING MATERIALS AND ASSOCIATED METHOD

BACKGROUND OF THE INVENTION

1. Field of the Invention

The present invention is directed toward a viscometer which permits determination of viscosity of an expanding foam material on the basis of axial pressure measurements and foam rise measurements and, more specifically, relates to such a system which employs motionless apparatus.

2. Description of the Prior Art

In recent years, numerous commercial uses have been made of polymeric foam materials. Among the numerous uses are, for example, uses in residential and commercial building products as thermal insulation, as well as other thermal insulation uses, as in refrigerators, and uses in automotive and household seating and bedding materials.

It has been known to use flexible, as well as foamed polyurethane, and phenolics, as well as other polymeric foams which are produced by casting in a mold.

Among the problems encountered in connection with such uses have been cell structure defects, excessive curvature or other deformations, undesired mold leakage, and undesired changes in density. In the past, efforts to obtain reliable information as to the molding properties of specific foamed synthetic resin precursor systems of a small-scale basis and extrapolating the results to large scale, have been generally unsuccessful. As a result, expensive, large-scale testing has been required.

Various means have been suggested for determining viscosities for plastics, in general, as distinguished from foamed plastics. U.S. Pat. No. 3,138,950 disclosed measurement of polymer melt viscosities through use of strain gauges. See also, U.S. Pat. No. 3,559,464 which discloses monitoring of a plastic in a Rheometer which employs two distinct capillaries of different length and associated pressure gauges in cooperation with a computer.

U.S. Pat. No. 3,194,057 disclosed a viscometer which employs ultrasonic waves and attenuation thereof as a means for measuring viscosity of fluids.

U.S. Pat. No. 3,360,986 relates to foaming plastics and a system wherein a predetermined volume chamber receives the plastics at a pressure which prevents foaming. A ram urges the plastic through the capillary and the time required for a particular quantity of the plastic to be extruded is recorded with the shear rate being determined.

U.S. Pat. No. 4,137,754 relates to a melt rheometer for measurement of flow properties of foamable plastics. The material is introduced into an extruder and mixed with a blowing agent which is introduced through a port. Movement of the piston coordinates feed of the blowing agent. The material is forced through a capillary orifice. Pressure transducers are employed.

A study of the basic heat balance of a foaming polyurethane system is disclosed in Campbell "Polyurethane Foam Process Development: A Systems Engineering Approach," Journal of Applied Polymer Science, Volume 16, Pages 1387–1402 (1972), but is believed by the present inventor to be in error in its assumption that the rate of evaporation as obtained from the heat balance could be converted directly into a rate of volume expansion which assumes uniform pressure distribution. This approach disregards the stress factor.

There remains, therefore, a very real and substantial need for a viscometer which will simply and economically provide accurate, small-scale results which are adapted to be used on a large-scale basis or, in the alternative, provide direct large-scale results, if desired.

BRIEF SUMMARY OF THE INVENTION

The present invention provides a motionless viscometer and associated method for use in connection with cast polymeric foams.

In a preferred embodiment, reservoir means contains the material to be foamed, receiver means is adapted to receive the expanded foamed material and interposed tube means serve to connect the reservoir means with the receiver means. Pressure sensing means are provided in the tube means in order to monitor the axial pressure of the expanding foam and rise measuring means are provided to determine the rate of rise of the expanding foam. In a preferred embodiment, the pressure sensing means includes one or more pressure transducers which convert the foam pressure into a corresponding electrical signal. The measurement of rise may be accomplished by an ultrasonic transducer of the depth monitoring type.

In the method of the present invention the reservoir means, receiver means and connecting tube means are provided. Foaming action is initiated with the result that the polymeric material will be expanded. The axial pressure is sensed within the tube means and the rate of rise is measured. On the basis of the axial pressure and rate of rise, the shear viscosity of the expanding material may be determined. It is an object of the present invention to provide a viscometer and associated method for use with resinous and non-resinous foaming materials in order to permit detailed determination of properties which will influence the success or failure of efforts to produce a cast product from the material.

It is a further object of the invention to provide such apparatus and method which is adapted to be employed on a small-scale basis which may readily be extrapolated to large-scale uses.

It is a further object of the present invention to provide such a system which will permit improved quality control of the techniques of making various products from the material.

It is a further object of the present invention which permits determination of shear viscosity as a means for determining process characteristics of the material.

These and other objects of the present invention will be more fully understood from the following disclosure on reference to the drawings appended hereto.

DESCRIPTION OF THE PREFERRED EMBODIMENTS

Figure 1:
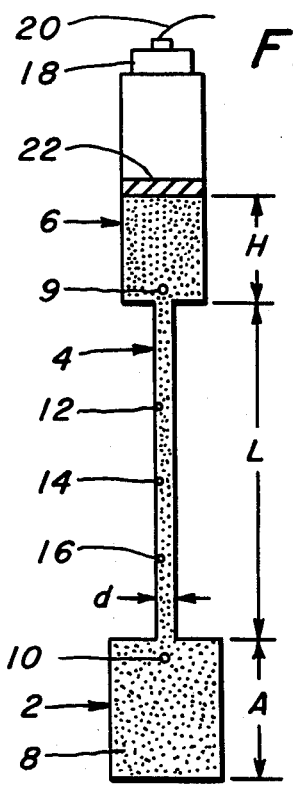
FIG. 1 is a schematic illustration of one form of apparatus of the present invention.

Referring now more specifically to FIG. 1, there is shown schematically, a form of apparatus adapted for use with the present invention. The apparatus is adapted to be used in a small-scale test which will provide results which correlate with full-scale commercial production. In the form illustrated, a reservoir 2 is adapted to contain the polymeric resin which will be foamed. Foaming action may be initiated by any desired means such as chemical means or by the addition of a physical blowing agent, for example. Foaming action may be initiated either prior to connecting the reservoir means to the rest of the apparatus or thereafter. In spaced overlying relationship with respect to the reservoir means 2 is a receiver means 6. In the form shown, a capillary tube 4 connects the reservoir means 2 with the receiver means 6 and permits communication therebetween. It will be appreciated that initiation of the foaming action will result in expansion of the polymeric foam material upwardly into the capillary tube and ultimately into the receiver means 6. It will generally be preferred to limit the unfoamed material to the reservoir means 2.

A series of pressure sensors, which in the form shown are pressure transducers 12, 14, 16 are spaced longitudinally along the capillary tube 4 and are operatively associated therewith in order to measure axial pressure of the expanding foam at several axial locations. While three such pressure sensors have been shown, it will be appreciated that a greater or lesser number may be provided if desired. Positioned in operative relationship with respect to the receiver means 6 is overlying, ultrasonic transducer 18 which may be of the depth finder type and is adapted to measure the rate of rise of the upper surface of the plastic material 8 as it expands within the receiver means 6. Electrical wire 20 transports an electrical signal emitted by the ultrasonic transducer responsively to the ultrasonic waves indication of distance between the transducer 18 and the upper surface of the foamed plastic 8. In the form shown, a float member 22 is provided as a reference for use with the ultrasonic transducer.

If desired, alternate means for monitoring rise of the foamed plastic could be employed. For example, movement of a float could be monitored through a transparent wall by a movie camera or float movement could be monitored by magnetic means.

Thermocouple means 9 are disposed within the lower reaches of receiver 6 in order to measure the temperature of the expanded foam 8. Similarly, thermocouple means 10 are positioned adjacent the exit means of the reservoir 2 to measure the temperature of the plastic foam.

The electrical signals corresponding to the information received by the pressure sensors 12, 14, 16, the ultrasonic transducer 18 and the thermocouples 9, 10 may be carried to suitable processing or readout equipment. For example, gauges which provide a visual indication of the signal, means for making a permanent record such as printers or computer means, for example, may be provided to record or process the data. In a preferred embodiment of the invention, it is desired to employ the axial pressure profiles obtained from the pressure sensors 12, 14, 16 in combination with the foam rise profile provided by successive readouts of ultrasonic transducer 18 in order to determine shear viscosity of the material.

The reservoir means 2, receiver means 6, and capillary means 4 may be made of any suitable inert material and so connected as to resist undesired leakage of the expanding plastic material therefrom. Among the suitable materials for these pieces of equipment are materials selected from the group consisting of steel, aluminum, polycarbonate and glass. For example, reservoir means 6 may be a cylindrical steel vessel having an inner diameter of 122 millimeters and a height A of 150 millimeters and is used as primary source of foam. It may be provided with a sealed aluminum lid 12.7 millimeters thick. A perspex thick-walled capillary of 12.7 millimeters, inner diameter, is installed in the center of the lid (not shown). Tests have been run with capillary tubes having a length L from 600 to 1500 millimeters in 300 millimeter increments. Strain gauge pressure transducers such as those sold under the trade designation Entran EPS-1032 are installed at $\frac{1}{4}$, $\frac{1}{2}$ and $\frac{3}{4}$ of the total axial length L of capillary tube 4. Temperatures at the inlet and outlet of the tube 4 are measured by the means of thermocouples 10, 9. After passage through the instrumented test section, the foaming mass is collected in a cylindrical receiver 6 which has an inner diameter of 92 millimeters. The foam rise is monitored using an ultrasonic depth measuring device such as that sold under the trade designation Crane Pro-Tech Model UDX. To facilitate the measurements of the foam rise to styrofoam float 22 is installed in the reservoir 6. Output signals from the pressure and ultrasonic transducers and from the thermocouples were registered using multichannel recorders such as those sold under the trade designation Houston Instrument, Omniscribe B-5000. A flexible urethane foam formulation such as has been used in automotive seat applications was used. The components were mixed in the reservoir 2 at about 14° C. After mixing, the reservoir 2 was attached to the capillary tube 4. After each test run the foam was removed from the apparatus and analyzed. The mixing equipment (not shown) preferably consists of a high speed stirrer with a brake. If desired, mixing may be accomplished by impinging jets of air or gas, impellers, magnetic stirrers or other means. The reservoir 2, the receiver 6, the capillary tube 4 were thoroughly cleaned and recoated with a lubricant material such as that marketed under the trade designation Teflon.

Depending upon the objectives of the particular test and whether the test is on a reduced scale or full scale basis, the dimensions of the components shown in FIG. 1 may be varied substantially. It will generally be preferred, however, that the length L of the capillary tube 4 be about 5 to 200 times the internal diameter d thereof. Also, it will be preferred to have the reservoir 2 and the receiver 6 generally cylindrical and having a diameter about 2 to 50 times greater than diameter d of tube 4. As shown in FIG. 1 at the point of illustration, the foamed plastic has risen in the receiver 6 to a level H. While for convenience of reference herein the tube means has been disclosed as being a generally cylindrical capillary tube 4, it will be appreciated that the tube means may be of other than circular, interior cross-sectional configurations. For example, it could be of triangular, rectangular or other geometric shape. In such context "d" may be considered to be the average internal dimension of the tube means. Also, while the disclosed embodiment has substantially uniform internal cross section throughout its axial extent and this is preferred, this is not essential and variations may be provided if desired. Also, the tube means need not have a straight axis and could, for example, be a coil, if desired.

As used herein, in the absence of an express indication to the contrary, reference to time refers to measurement taken from the instant action has been taken to initiate foaming of the plastic. For example, in connection with a chemically activated foaming action where isocyanates are employed to trigger first foaming, time would be measured from the point in time when the isocyanates are added.

I have determined certain relationships which exist between the properties of the foamed plastic material. The foam's apparent viscosity is sufficiently high in the tests of the apparatus illustrated in FIG. 1 as to give a Reynolds number of substantially less than 1 or negligible. Also, changes in momentum due to the unsteady nature of the flow are small compared with the viscous shear forces beyond the initial developing stages of flow. The flow rate along tube 4 is nearly constant where the tube diameter d is substantially less than the diameter of reservoir 2.

The mean density can be determined from the ultrasonic transducer readings (1) mean density $= M/(V_1 + V_T + P_i R^2_H)$ where M is the total initial mass of the resin and the other materials which trigger the foaming action. $V_1$ and $V_2$ are volumes respectively of the reservoir 2 and the tube 4. R is the radius of the receiver 6 and H is the instantaneous foam height H in the reservoir 6 as measured by the ultrasonic transducer 18, for example.

To compute the flow rate as a function of time, the following relationship may be employed:

$$Q = -\frac{V_1}{\text{mean density}} \times \frac{d(\text{mean density})}{dt} \text{ wherein } Q \quad (2)$$

is the flow rate.

The apparent or shear viscosity may be determined by the following formula:

Shear Viscosity = (Apparent Shear Stress/Shear Rate)

The apparent shear stress is equal to the pressure drop per unit length of the instrumented portion of the tube 4 multiplied by r/2 where r is the radius of the tube 4. Shear rate is equal to $4Q/\pi i r^3$.

Figure 2:
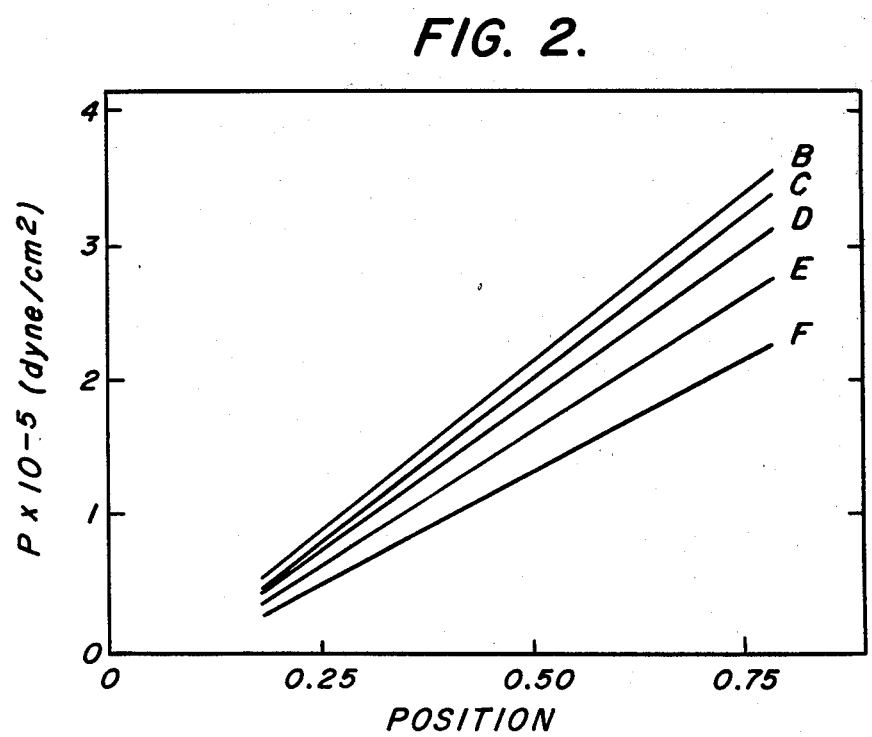
FIG. 2 is a plot of pressure versus distance taken at several different times after initiation of foaming action.

Referring now in greater detail to FIG. 2, there is shown a plot of pressure $\times 10^{-5}$ as measured along capillary tube 4 with the units being dyne/centimeter squared as against axial position of the point of measurement within the capillary tube. The digital references on the x axis refer to the ¼, ½ and ¾ positions axially within the tube 4 from the top end of the tube. The pressure measurements were taken at points ¼, ½ and ¾ of the axial extent of the capillary tube 4 by means of pressure transducers 12, 14, 16 and the results were extrapolated. It is noted that the relationship is linear. As the axial pressure profile is linear over a broad time interval, this indicates the properties of the foaming mass are virtually independent of the axial position within the tube 4 and the flow rate along the tube is nearly constant. Plot B represents measurements taken at t = 114 seconds, plot C measurements taken at t = 102 seconds, plot D measurements taken at 90 seconds, plot E measurements taken at 78 seconds and plot F measurements taken at 66 seconds. It is noted that the slope of each plot B, C, D, E, F is greater as the time increases. This reflects the increase in viscosity with the passage of time.

Figure 3:
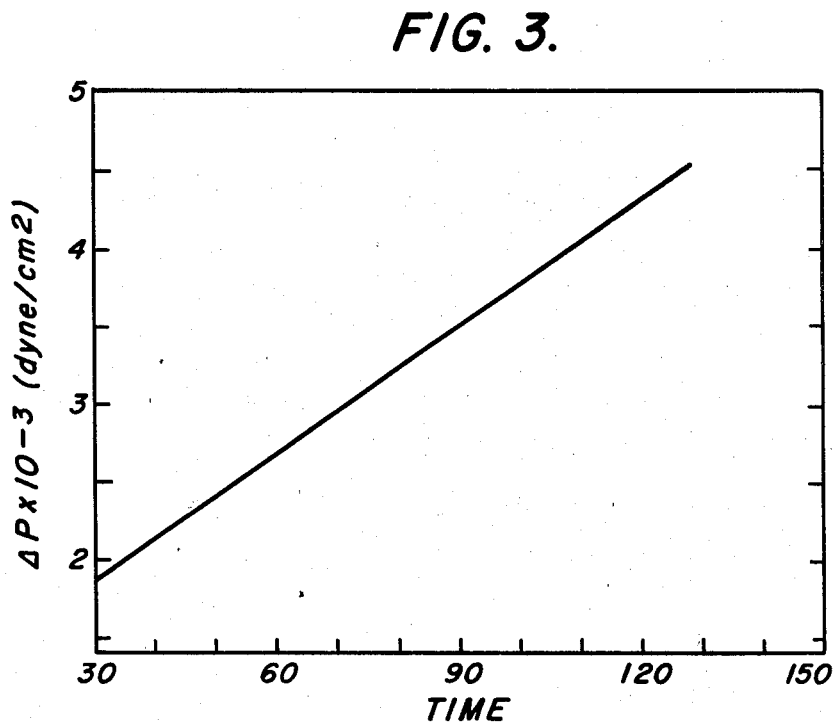
FIG. 3 is a plot of pressure versus time.

Referring now to FIG. 3, there is shown a plot of the change in pressure with change in distance along the capillary tube (pressure gradient) $\times 10^{-3}$ in units of dyne/centimeter squared as against time in seconds. It is noted that the curve is linear.

Figure 4:
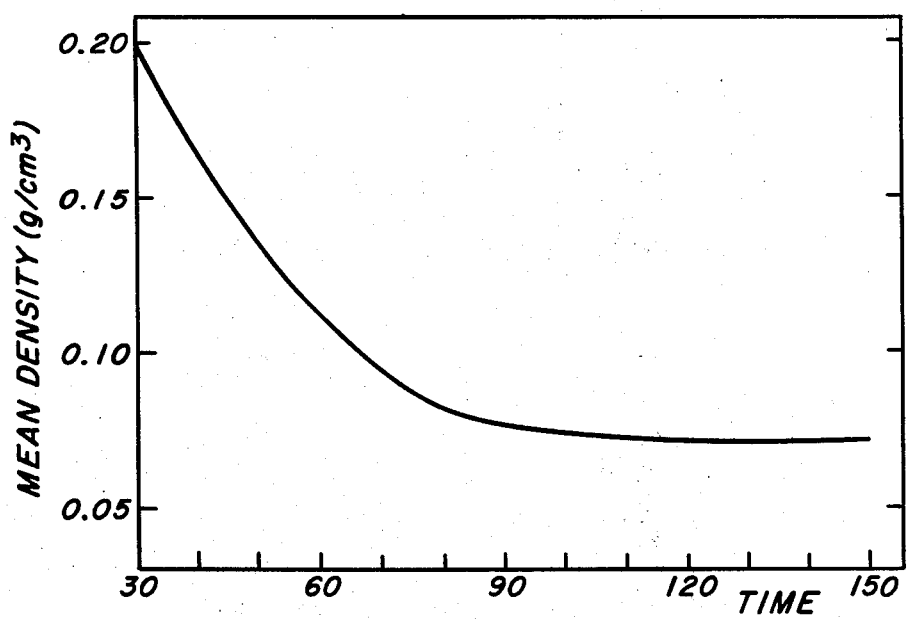
FIG. 4 is a plot of mean density of the polymeric foam as a function of time.

Referring now to FIG. 4 in greater detail, this is a plot of the mean density in gram/cubic centimeter versus time in seconds. With the expansion of the individual cells as the plastic foams, the mean density declines with the passage of time. Generally adjacent to the 150 second mark the expansion process has ceased and as a result, the mean density has reached a point of stability.

Figure 5:
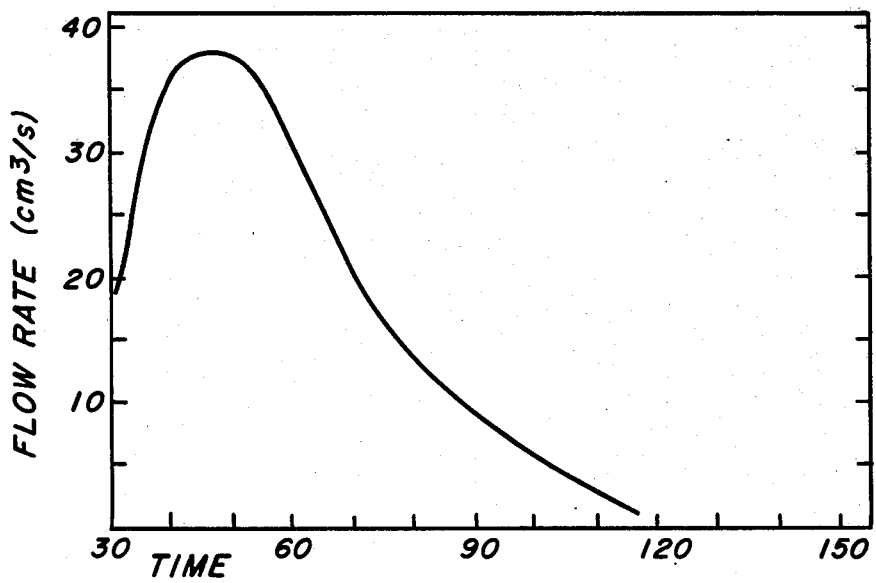
FIG. 5 is a plot of volumetric flow rate as a function of time.

Referring now to FIG. 5 in greater detail, there is shown a plot of flow rate in cubic centimeters/second versus time in seconds. It will be seen that there is an initial sharp climb in flow rate and a rather steep decline after.

Figure 6:
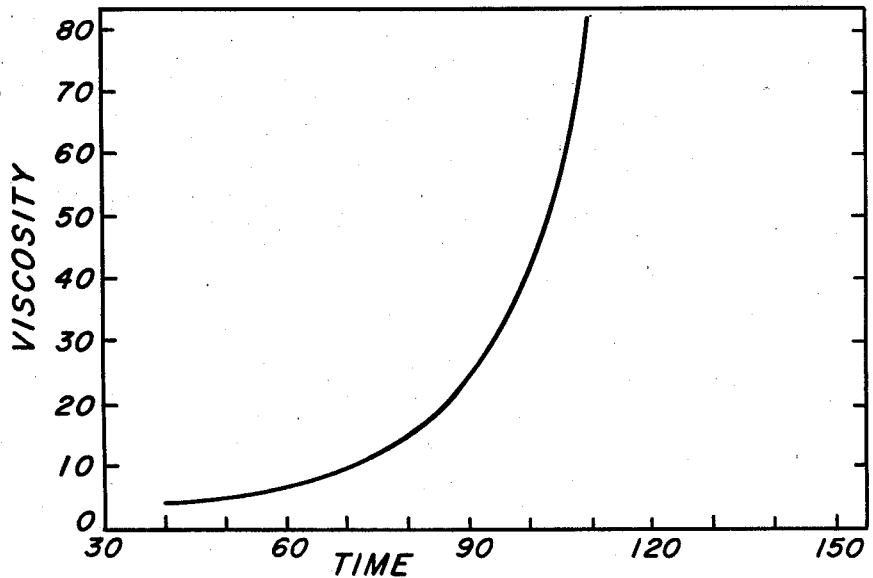
FIG. 6 is a plot of viscosity as a function of time.

Referring now in greater detail to FIG. 6, there is shown a plot of shear viscosity in poise versus time in seconds. This plot of shear viscosity has been obtained on the basis of the pressure profile as shown in FIG. 2 (corresponding to the measurement of axial pressure in capillary tube 4) and the flow rate as illustrated in FIG. 5 corresponding to the rate of rise measured by ultrasonic transducer 18.

It will be appreciated, that as a result of the measurement of axial pressure and rate of rise, the shear viscosity which has a marked influence on the resultant properties in the cast foam product may be determined by the apparatus and process of the present invention. The present apparatus and method, therefore, permit foam formation analysis as a macroscopic flow problem. For a given set of physico-chemical, geometrical and operational parameters, the flow characteristics can be specified fully be measurement of the foam rise and the pressure profile in the mold. This data can be converted into time dependent density and viscosity as well as shear sensitivity determinations.

Whereas a specific geometric form of apparatus and related process has been disclosed for purposes of illustration, it will be appreciated that various configurations will be apparent to those skilled in the art. Also, while specific mention has been made of certain foaming materials, it will be appreciated that the invention is adapted for use with a wide range of foamable resinous and non-resinous materials such as baking products, for example.

Whereas the tube means and receiver means have been illustrated as separate elements secured to the assembly with the former containing the pressure sensing means and the latter permitting monitoring of rise, it will be appreciated that, if desired, the members may be provided as a functional unit either through manufacture as such or assembly as such.

Whereas particular embodiments of the invention have been disclosed herein for simplicity of disclosure and convenience of reference, it will be apparent that those skilled in the art may make alterations in the apparatus and method without departing from the scope of the invention as set forth in the claims herein.

I claim:

1. A viscometer for foaming materials comprising
reservoir means for containing a supply of material to be foamed,
receiver means for receiving a portion of the foamed material, pressure sensing means for measuring the pressure of said material as it is foamed, and rise measuring means operatively associated with said receiver means for measuring the rate of rise of said foaming material within said receiver means.

2. The viscometer of claim 1 including tube means connecting said reservoir means with said receiver means.

3. The viscometer of claim 2 including said pressure sensing means being operatively associated with said tube means.

4. The viscometer of claim 2 including said tube means being a tube having a maximum transverse dimension less than the maximum transverse dimension of either said reservoir means or said receiver means.

5. The viscometer of claim 2 wherein said tube means include a capillary tube.

6. The viscometer of claim 5 including said tube means being of substantially uniform internal diameter throughout its longitudinal extent.

7. The viscometer of claim 2 including said rise measuring means including transducer means for monitoring movement of the upper surface of said polymeric foam and emitting responsive electrical signals.

8. The viscometer of claim 7 including said transducer means being an ultrasonic transducer depth measuring device.

9. The viscometer of claim 8 including said rise measuring means including float means for cooperating with said ultrasonic transducer depth measuring device in determining the movement of said upper surface.

10. The viscometer of claim 2 including said pressure sensing means including at least one pressure transducer for sensing pressure within said tube means and emitting a responsive electrical signal.

11. The viscometer of claim 10 including temperature sensing means operatively associated with said receiver means and said reservoir means for measuring the temperature of said foam.

12. The viscometer of claim 11 including said temperature sensing means including thermocouple means.

13. The viscometer of claim 10 including said pressure sensing means including a series of axially spaced pressure transducers.

14. The viscometer of claim 10 including said reservoir means and said receiver means have an average transverse extent of about 2 to 50 times the average transverse extent of said tube means.

15. The method of testing polymeric foams of claim 1 including determining said viscosity and density as functions of time.

16. A method of testing foaming materials comprising providing reservoir means for containing a supply of material to be foamed and receiver means for receiving the polymeric foam, initiating foaming action, sensing the pressure of said expanding foam, measuring the rate of rise of said expanding foam in said receiver means, and employing said pressure and said rate of rise to determine viscosity of the foaming material.

17. The method of claim 16 including employing said method in connection with polymeric foaming materials and employing said method to determine shear viscosity of said foaming material.

18. The method of claim 17 including providing tube means, and sensing said pressure in said tube means.

19. The method of testing polymeric foams of claim 16 including employing pressure transducer means to measure said pressure.

20. The method of testing polymeric foams of claim 19 including employing ultrasonic transducer depth finding means to measure said rate of rise.

21. The method of testing polymeric foams of claim 16 including measuring the temperatures of said foam within said reservoir means and within said receiver means.

* * * * *